United States Patent
Myerson et al.

(10) Patent No.: US 6,759,521 B2
(45) Date of Patent: Jul. 6, 2004

(54) POLARIZATION SWITCHING TO CONTROL CRYSTAL FORM

(76) Inventors: Allan S. Myerson, 1450 W. Summerdale Ave., 1-E, Chicago, IL (US) 60640; Bruce A. Garetz, 95 Reade St., New York, NY (US) 10013

( * ) Notice: Subject to any disclaimer, the term of this patent is extended or adjusted under 35 U.S.C. 154(b) by 58 days.

(21) Appl. No.: 09/965,751

(22) Filed: Sep. 28, 2001

(65) Prior Publication Data

US 2002/0120105 A1 Aug. 29, 2002

Related U.S. Application Data

(63) Continuation-in-part of application No. 09/694,404, filed on Oct. 23, 2000, now Pat. No. 6,426,406.

(51) Int. Cl.[7] ............................. B01D 9/02; C07K 1/30
(52) U.S. Cl. ................ 530/418; 23/295 R; 204/157.15; 204/157.51; 204/157.61; 204/157.68; 204/157.69; 204/157.75; 204/157.82; 204/157.87; 204/157.9; 204/158.14; 530/427; 562/575
(58) Field of Search ....................... 23/295 R; 562/575; 530/418, 427; 204/157.15, 157.41, 157.61, 157.68, 157.69, 157.75, 157.82, 157.87, 157.9, 158.14

(56) References Cited

U.S. PATENT DOCUMENTS

| 5,976,325 | A | | 11/1999 | Blanks ................... 204/157.41 |
| 6,426,406 | B1 | * | 7/2002 | Myerson et al. ............ 530/418 |
| 6,596,077 | B2 | * | 7/2003 | Myerson ....................... 117/68 |
| 2003/0024470 | A1 | * | 2/2003 | Myerson ....................... 117/68 |
| 2003/0101926 | A1 | * | 6/2003 | Myerson ....................... 117/84 |

OTHER PUBLICATIONS

The Merck Index, Eleventh Ed. Rahway: Merck & Co. Inc., pp. 57, 1553 (1989).*

Garetz, B.A., et al., Nonphotochemical, Polarization–Dependent, Laser–Induced Nucleation in Supersaturated Aqueous Urea Solutions, Physical Review Letters, Vo. 77, No. 16, pp. 3475–3476 (1996).

* cited by examiner

*Primary Examiner*—Jeffrey Edwin Russel
(74) *Attorney, Agent, or Firm*—Technoprop Colton LLC (57) ABSTRACT

A method to select and prepare polymorphs of materials by switching the polarization state of light employing non-photochemical laser-induced nucleation.

49 Claims, 9 Drawing Sheets

POLARIZATION SWITCHING TO CONTROL CRYSTAL FORM

CROSS-REFERENCE TO RELATED APPLICATION

The present invention is a continuation-in-part of U.S. patent application Ser. No. 09/694,404, filed on Oct. 23, 2000, which issued as U.S. Pat. No. 6,426,406 on Jul. 30, 2002.

BACKGROUND

1. Field of the Invention

This invention relates generally to the field of inducing the nucleation of selected crystal polymorphs from supersaturated solutions and specifically to a process of inducing the nucleation of selected crystal polymorphs from supersaturated solutions by using laser light to induce nucleation, and switching the polarization of the laser light to select a particular crystal polymorph. This invention further relates to the ability to change the crystal polymorph induced by laser nucleation by switching the polarization from linear to circular to elliptical, thus allowing the selection of a particular polymorph, whether stable or metastable.

2. Prior Art

The crystal structure of a material determined by x-ray diffraction gives a complete picture of the arrangement of the atoms (or molecules) of the chemical species in the crystalline state. It is possible, however, for a given chemical species to have the ability to crystallize into more than one internally distinct structure. This ability is called polymorphism (or allotropism if the species is an element). Different polymorphs of the same material can display significant changes in their properties as well as in their structure.

The term polymorphism is contrasted with morphology. Crystals are solids with the atoms, molecules, or ions in a regular repeating structure. The overall external form is referred to as crystal morphology. The term morphology refers to the external shape of the crystal and the planes present, without reference to the internal structure. Crystals obtained experimentally can display different morphology based on different conditions, such as, for example, growth rate, stirring, and the presence of impurities. In contrast, as stated above, polymorphism refers to the internal alignment and orientation of the molecules. A substance can have several distinct polymorphs and only one morphology, or can have several distinct morphologies for only one polymorph. A change in morphology does not imply that a new polymorph arises, and vice versa. Unlike with different morphologies, one cannot tell by visual inspection whether one has a different polymorph.

The prior art is directed to nucleating substances to achieve a desired morphology and crystal structure that is known to arise under the given set of conditions. There is no discussion in the prior art of using specifically polarized light to achieve crystallization or a specific crystal polymorph. Further, there is no discussion in the prior art of nucleating a new or unknown crystal structure (a new polymorph) or of an unexpected structure (a known polymorph that would not normally occur under these conditions). It is important to note that crystals of a given substance with different morphologies (external shape) have the same physical properties (such as melting point, solubility, electrical conductivity, etc) while different polymorphs (internal structure) of the same substance have different properties (e.g., diamond and graphite, which are different polymorphs of carbon).

Polymorphism is quite common in the elements and in inorganic and organic compounds and results in property changes. A dramatic example is carbon, which can crystallize as graphite or as diamond. Diamond is a cubic crystal, whereas graphite is a hexagonal crystal. In addition, properties such as hardness, density, shape, vapor pressure, dissolution rate, and electrical conductivity are all quite different for these two solids. These major differences in the properties of two polymorphs are not unique to carbon and can occur in all materials that display polymorphism. Many of the early identifications of polymorphs were minerals, such as calcium carbonate, which has three polymorphs (calcite, aragonite, and vaterite) and zinc sulfide, which has three polymorphs (wurtzite, sphalerite, and matraite). Some well known species have large numbers of polymorphs, for example water, which has eight different solid forms of ice. Organic molecular crystals often have multiple polymorphs that can be of great significance in the pharmaceutical, dye and explosives industries.

Under a given set of conditions, one polymorph is the thermodynamically stable form. This does not mean that other polymorphs cannot exist or form at these conditions, only that one polymorph is stable and other polymorphs present within the solution can transform to the stable form. An example of this can be seen in heating (or cooling) a crystalline material with multiple polymorphs. As the temperature changes, the material can eventually enter a region where another polymorph is the stable form. The transformation of one polymorph to another, however, will occur at some rate that may be rapid or very slow. The transformation rate varies because the rate of transition of polymorphs depends on the type of structural changes that are involved.

Transformations can be categorized by the types of structural changes involved, which can roughly be related to the rate of transformation. For example, a transformation in which the lattice network is bent but not broken can be rapid. This type of transformation is known as displacive transformation of secondary coordination. Another type of rapid transformation can involve the breakage of weaker bonds in the crystal structure with the stronger bonds remaining in place. This is then followed by the rotation of parts of the molecule about the structure and the formation of new bonds. This type of transformation is a rotational disorder transformation. Slow transformations usually involve the breakage of the lattice network and major changes in the structure or type of bonding.

Polymorphic transformations also can be classified as first- or second-order transitions. In a first-order transition, the free energies of the two forms become equal at a definite transition temperature, and the physical properties of the crystal undergo significant changes upon transition. In a second-order transition, there is a relatively small change in the crystal lattice, and the two polymorphic forms will be similar. There is no abrupt transition point in a second order transition, although the heat capacity rises to a maximum at a second order transition point.

When a material is crystallized from solution, the transition between polymorphs can occur at a much higher rate because the transition is mediated by the solution phase. Polymorphs of a given material will have different solubilities at a given temperature, with the more stable polymorph having a lower solubility (and a higher melting point) than the less stable polymorph. If two polymorphs are in a saturated solution, the less stable polymorph will dissolve and the more stable polymorph will grow until the transition is complete. The rate of the transition is a function of the difference in the solubility of the two forms and the overall degree of solubility of the compounds in solution. This transition requires that some amount of the stable polymorph be present, meaning that the stable polymorph must nucleate at least one crystal for the transition to begin. If a slurry of solution and crystals of a polymorph stable at a high temperature is cooled to a lower temperature, where another polymorph is the stable phase, the transition of the crystals already present will depend on the presence of nuclei of the new stable phase. The more of these nuclei present, the faster the transition will occur.

Another interesting feature of organic molecular crystals is that the molecular conformation (the shape of the molecule) of a species can be different in two polymorphs of the same material. The same molecule can display different shapes (conformations by rotations about single bonds for example). Conformational polymorphism is the existence of polymorphs of the same substance in which the molecules present are in different conformations.

It is known that by subjecting some supersaturated solutions to laser light, the onset of nucleation occurs. Prior to nucleation, the supersaturated solution contains clusters of molecules that are not arranged in the lattice structure of a crystal. The laser light helps to align or organize the molecules in the clusters into a lattice arrangement resulting in the formation of nuclei and, after time, crystals. For a urea solution, it was shown that the laser could induce nucleation and the one and only known and expected polymorph for urea was obtained. Garetz, B. A. et al., Nonphotochemical, Polarization-Dependent, Laser-Induced Nucleation in Supersaturated Aqueous Urea Solutions, *Physical Review Letters*, Vol. 77, No. 16, pp. 3475–6 (1996).

In the Garetz article, it was shown that pulses from a Q-switched Nd:YAG laser could induce nucleation in supersaturated solutions. In the case of urea, the crystallites that are formed have the same structure as crystallites that form when the same solution spontaneously nucleates. After supersaturated solutions with concentrations in the range of 11.5–13.5M were aged for one to two weeks, the solutions were illuminated with the 1.06-$\mu$m wavelength, plane-polarized output of a Quanta-ray DCR-1 Q-switched Nd:YAG laser. A portion of the doughnut-shaped beam with approximately constant intensity was selected by passing the beam through an aperture with an area of ~2 mm$^2$. With the laser oscillator alone, the measured energy per pulse was 0.02 J, while with the amplifier added, it was 0.1 J. The measured pulse width was 20 ns, and the pulse repetition rate was 10 pps. The unamplified and amplified pulses thus had intensities of 50 and 250 MW/cm$^2$, respectively. Exposure of the aged solutions to laser pulses from the oscillator alone was not sufficient to induce nucleation. With the amplifier added, nucleation typically occurred within 10–20 s.

The urea solutions reported in Garetz are highly transparent at the laser wavelength of 1.06 $\mu$m, so that photochemical effects are improbable. Therefore, the most likely candidates for laser-solution interactions are electric-field effects, such as the optical Kerr effect or electrostriction. The applied electric field apparently aids in organizing existing pre-nucleating clusters, increasing the chances that one will nucleate and grow.

The Garetz article does not disclose switching the polarization of the light either to cause the nucleation of a desired specific polymorph or to cause the creation of an unexpected (new) polymorphs, as disclosed and claimed in the present patent application. Importantly, as stated, urea has only one polymorph, which will be the polymorph in solution in the advent of nucleation. Therefore, it does not matter in the Garetz article process which polarization state is used—both should result in the single known urea polymorph. More specifically, the Garetz article discloses the effect laser-induced nucleation has on the orientation of the molecules and that the polarization dependence of the crystallite orientation is consistent with a mechanism in which the electric field of the light plays a major role and that urea molecules are being aligned by the applied optical field, just as they are in the optical Kerr effect, also known as light-induced birefringence. The Garetz article further discloses that only urea's anisotropic polarizability is responsible for electric-field-induced alignment at optical frequencies, thus, according to the Garetz mechanism, urea molecules in a cluster will tend to align with their $C_2$ rotation axes parallel to an applied electric field, E, growing into a crystallite with the needle axis parallel to E.

The discovery published in the Garetz article is a photophysical phenomenon in which the laser induced crystallization of urea causes the alignment of the urea molecules by the applied optical field. The crystals that result from the experimentation disclosed in the Garetz article were known and expected crystals. The novelty of the Garetz article is that the laser light causes the urea molecules to align, facilitating the nucleation into the known crystals. This is substantially different from the present invention, which is the creation of unexpected and/or new polymorphs not normally obtained using current art nucleation methods by switching the polarization of the incident light. Most importantly, the Garetz article does not disclose a relation between the polarization of light source and polymorphs.

U.S. Pat. No. 5,976,325 to Blanks discloses a method for producing a substance with a known morphology and crystal structure in aluminate solution. Blanks '325 discloses a self-seeding process to obtain the most stable crystal structure of sodium aluminate from a supersaturated aluminate solution (i.e. Bayer Process solution) and does not implicate the polymorphism of the substance. More distinctively, the process in Blanks '325 is primarily for destroying impurities in the solution, and the light used is absorbed by the materials.

Blanks '325 discloses a process for forming a precipitated alumina hydrate, comprising the steps of providing a sodium aluminate solution; and illuminating said sodium aluminate solution with light wave energy produced by the near infrared wavelength, linearly polarized output of a laser to form a precipitated alumina hydrate where no external seed is added. Much like the Garetz article, Blanks '325 discloses a method for obtaining a known crystal in a process for forming a precipitated alumina hydrate such as aluminum trihydroxide by providing a supersaturated sodium aluminate solution and treating the solution by illumination with pulsed near infrared light wave energy, spatially and temporally overlapped inside the solution, so as to produce a photo-induced nucleation of purified gibbsite crystals, without the need for external seed.

Blanks '325 does not disclose or claim, or even discuss, the formation of different or unexpected polymorphs through the switching of the polarization state of the incident light. Blanks '325 does not disclose whether a specific polymorph of alumina hydrate is desired and, more importantly, whether a different polymorph of alumina hydrate that is not typically created for use in the purification process (or an unknown polymorph of alumina hydrate) is created or can be created by switching the polarization state of the light.

Blanks '325 discloses a laser treatment process for introducing infrared light into green Bayer liquor to provide enhancements in alumina yield of as much as 50 grams/liter without the addition of seed. This, coupled with the lack of disclosure on how to prepare different or unknown polymorphs, and polymorphs that normally would not result under the same conditions without the use of the selected light, or to switch the polarization state of the light to obtain a different polymorph, indicates that Blanks '325 does not contemplate the present invention.

The mechanism by which the Blanks '325 method works also is different than that of the present patent application. Blanks '325 discloses that the laser removes undesirable organic compounds that are generally considered as inhibitors to alumina hydrate precipitation. In other words, the laser works by photochemically destroying organic impurities, thus permanently changing the conditions (i.e., with inhibitors removed) under which the nucleation proceeds. The method therefore requires that the laser light be absorbed by organic impurities in the solution, so that in Blanks '325 the wavelength of the laser needs to be tuned to match the absorption bands of the organic impurities in their samples. One feature of Blanks '325 is that by absorbing near infrared light, they are able to induce the photochemistry needed to destroy their organic impurities. In contrast, the present invention involves essentially no light absorption by the sample.

Therefore, it can be seen that there exists a need for a process for selectively nucleating and creating known polymorphs of known substances and for nucleating and creating new polymorphs of known substances for use in laboratory and industrial settings. It is to this need that the present invention is directed.

BRIEF SUMMARY OF THE INVENTION

Crystallization from solution occurs from a supersaturated solution. Supersaturated solutions are metastable, meaning that they sometimes will not spontaneously crystallize. This is particularly true for organic molecular crystals because of the difficulty the molecules have in finding the correct lattice positions needed to form a solid crystalline material.

Briefly, the present invention is a novel method for creating new or unexpected polymorphs of known substances by means of irradiating a solution with a selected polarization of light. It has been found that switching the polarization of the light used in laser-induced non-photochemical nucleation can result in the creation of different polymorphs. For example, using light having linear polarization can result in the nucleation of a first polymorph, using light having circular polarization can result in the nucleation of a second polymorph, and using light having elliptical polarization may result in the nucleation of a third polymorph. Further, the method is repeatable, with a specific polymorph arising from the use of one polarization state, a different specific polymorph arising from the use of a second polarization state, and possibly a different specific polymorph arising from the use of a third polarization state.

Further, this invention has the potential for creating new polymorphs having internal crystal structures that are different than those of currently known polymorphs (new polymorphs) or different than what would be expected by one of ordinary skill in the art without use of the present method (unexpected polymorphs). Surprisingly, the new or unexpected polymorphs can be created without essentially chemically affecting or influencing the solution (that is, changing the chemistry of the solution).

In effect, the present method is a non-chemical method of affecting the solution. This can be important in both the laboratory and in industry. Because different polymorphs have different solid properties, different polymorphs behave differently when used for applications. For examples, a different polymorph of a dye would give a different color, and different polymorphs of drugs can have different bioavailability and dissolution properties. Much effort is spent in trying to find if a particular substance has additional polymorphs and in trying to prepare a particular polymorph. Developing and producing new polymorphs provides significant advantages both to research facilities and to commercial manufacturers, as both constantly are attempting to develop new products having better properties through the use of polymorphs.

This invention makes use of high-intensity pulses of laser light to induce nucleation in a supersaturated solution of a known substance. By subjecting the supersaturated solutions to laser light, the onset of nucleation occurs. By switching the polarization state of the light, different polymorphs can be created. That is, using one polarization state of the laser light can produce one polymorph, while using a different polarization state of the laser light can produce a different polymorph. Depending on the system, macroscopic crystals form on, for example, a timescale of seconds (aqueous urea) to hours (aqueous glycine).

Although various different types of lasers are suitable for this process, the preferred laser light is at near-infrared wavelengths, where many solutions are transparent, minimizing the absorption between laser and solution. More likely interactions involve responses of molecules to the electric field associated with the laser light, such as the optical Kerr effect (the field-induced alignment of molecules) or electrostriction (the field-induced movement of molecules into regions of high electric field). In each of these interactions, the electric field of the light polarizes a molecule, meaning that it applies forces to the electrons and nuclei that comprise the molecule, and induces transient changes in the charge distribution in the molecule. Whatever the interactions between light and molecule, they aid in the formation of an ordered cluster of molecules that goes on to grow into a crystal.

The present invention also can be used to cause the nucleation and crystal growth to occur in such a way as to obtain a crystal polymorphism that is unexpected under given conditions by the person of ordinary skill in the art. Previously, under a defined set of conditions, specific polymorphs will be present in the solution and will be known and expected by the person of ordinary skill in the art and a variation in the defined conditions can change the expected and known polymorph. However, the present method can be used to prepare new polymorphs of material that would not ordinary be observed to occur or prepare polymorphs that are not expected by the person of ordinary skill in the art to occur under given conditions in the absence of the method, simply by switching the polarization state of the light.

One feature of this invention generally is the use of laser light to induce the nucleation of a polymorph from a supersaturated solution that is different from the polymorph that would spontaneously nucleate from the supersaturated solution under the same general conditions, but in the absence of the selected polarization of the laser light.

Another feature of this invention is the use of continuous wave or pulsed lasers, in various polarization states (e.g., plane polarization versus circular polarization versus elliptical polarization), at various wavelengths where the supersaturated solution does not absorb, at various laser powers, pulse lengths, pulse repetition rates and exposure times, to induce the nucleation of a polymorph from a supersaturated solution that is different from the polymorph that would spontaneously nucleate from the supersaturated solution under the same general conditions, but in the absence of the selected polarization of the laser light.

Another feature of this invention is the use of various different process conditions (i.e., at various temperatures depending on the solubility of the compound being subjected to the light, various aging times, various supersaturation levels; various methods of achieving supersaturation such as cooling, heating, solvent evaporation, and changing solvent composition; and various different solvents such as organic or inorganic solvents) to induce the nucleation of a polymorph from a supersaturated solution that is different from the polymorph that would spontaneously nucleate from the supersaturated solution under the same general conditions, but in the absence of the selected laser light.

Another feature of this invention is to provide a method for inducing an unknown and/or unexpected polymorph and spontaneous nucleation in a solution under a set of conditions through the use of a laser light without essentially changing the chemistry of the solution.

These features, and other features and advantages of the present invention will become more apparent to those of ordinary skill in the art when the following detailed description of the preferred embodiments is read in conjunction with the attached figures.

DETAILED DESCRIPTION OF THE PREFERRED EMBODIMENTS

Theoretical

Crystallization from solution has great technological importance, as it used to separate and purify industrially significant substances such as pharmaceuticals, dyes, explosives and photographic materials. The use of laser light to induce nucleation has the potential of significantly reducing the nucleation time of crystals. This photophysical phenomenon is termed non-photochemical laser-induced nucleation (NPLIN) by the current inventors to distinguish it from the more familiar visible or ultraviolet light-induced nucleation that is based on a photochemical mechanism. An interesting feature of NPLIN is that the solution must be aged in order to exhibit the effect. A newly prepared solution will not undergo NPLIN. A supersaturated solution is a non-equilibrium system, and therefore its properties can change with time. A number of experiments, including diffusion, light scattering, and NPLIN all suggest that the average solute cluster size increases with time. These experiments suggest that NPLIN requires the presence of larger solute clusters, and, by acting on such clusters, is accelerating the rate-limiting organizational step of nucleation.

The inventors have observed NPLIN in a variety of aqueous solutions of small organic molecules, such as L-alanine, adipic acid, L-glutamic acid and succinic acid. One interesting case is glycine ($NH_2CH_2COOH$), which is known to exist in three distinct crystal structures (polymorphs) known as $\alpha$, $\beta$ and $\gamma$-glycine. Different polymorphs of the same compound can result in solids with great differences in physical and chemical properties, such as melting point, hardness, solubility, dissolution rate and bioavailability. Therefore the control of polymorph structure is a problem of technological importance. Living organisms are able to control the crystal phase and morphology of crystals through biomineralization. The growth of crystal surfaces can be enhanced or inhibited by the addition of tailor-made additives: impurity molecules that exhibit stereospecific interactions not unlike enzyme-substrate interactions.

The extremely strong intermolecular forces (dipole—dipole and hydrogen bonding) that exist between glycine molecules result in the presence of strongly bound groups of molecules (dimers, trimers, . . . , n-mers) that could behave as rigid entities in their response to an applied field. Some of these groups would resemble the structural building blocks of $\alpha$-glycine, and others the building blocks of $\gamma$-glycine. For example, a cyclic dimer is the basic unit of the double planes of molecules seen in $\alpha$-glycine, while a helical dimer is the basic unit of the hexagonally-packed helical chains of $\gamma$-glycine. There would exist a distribution of these n-mers in any liquid-like cluster of glycine molecules. The larger these n-mers, the more they would resemble the double planes and helical chains of $\alpha$- and $\gamma$-glycine respectively. The larger n-mers would therefore have exaggerated anisotropic polarizabilities compared to an individual glycine molecule, with the longer helical chains having rod-like polarizabilities, and larger double-planes having disk-like polarizabilities.

The orientation distribution, $f(\Omega)$, of a collection of anisotropically polarizable molecules or n-mers at temperature, T, resulting from its interaction with an applied optical field, E, can be calculated from the expression $f(\Omega)=\exp[E \bullet \alpha(\Omega) \bullet E/2\ kT]$, where $\alpha(\Omega)$ is the polarizability tensor of molecule or n-mer whose molecular axes $\{a, b, c\}$ are oriented at angles $\Omega=\{\theta, \phi, \psi,\}$ with respect to a laboratory reference frame $\{x, y, z\}$, and k is the Boltzmann constant.

For simplicity, in the case that the polarizability tensor can be represented by an ellipsoid of revolution, where a is the rotation axis, is used as an example. In that case, in the molecular reference frame, the tensor is diagonal with elements $\alpha_a$ and $\alpha_b=\alpha_c$. For linearly polarized alignment with E in the z direction, the resulting distribution is uniaxial and, to order $E_0^3$, is given by:

$$f_{lp}(\theta)=1+(E_0^2/4kT)\,[\alpha_a\cos^2\theta+\alpha_b\sin^2\theta],$$

where $\theta$ is the angle between the molecular a-axis and the laboratory z-axis. For circularly polarized alignment, with E rotating in the x-y plane, the distribution is also uniaxial and, to order $E_0^3$, is given by:

$$f_{cp}(\theta)=1+(E_0^2/8kT)\,[\alpha_a\sin^2\theta+\alpha_b(1+\cos^2\theta)].$$

These distribution functions can be characterized by the order parameter $K_z=<\cos^2\theta>$, reflecting the degree of alignment of the molecular a-axis in the laboratory z-direction. $K_x$ and $K_y$ are related order parameters that reflect the degree of alignment of the molecular a-axis in the laboratory x- and y-directions respectively. $K_z$ is equal to 1 for perfect z-alignment, 0 for complete x-y alignment, and $\frac{1}{3}$ for an isotropic distribution. For linearly polarized and circularly polarized electric-field-induced alignments, $K_z$ is, to order $E_0^3$, given by:

$$K_z^{lp}=\tfrac{1}{3}+(E_0^2/45kT)(\alpha_a-\alpha_b);\ K_z^{cp}=\tfrac{1}{3}-(E_0^2/90kT)(\alpha_a-\alpha_b)$$

Figure 9:
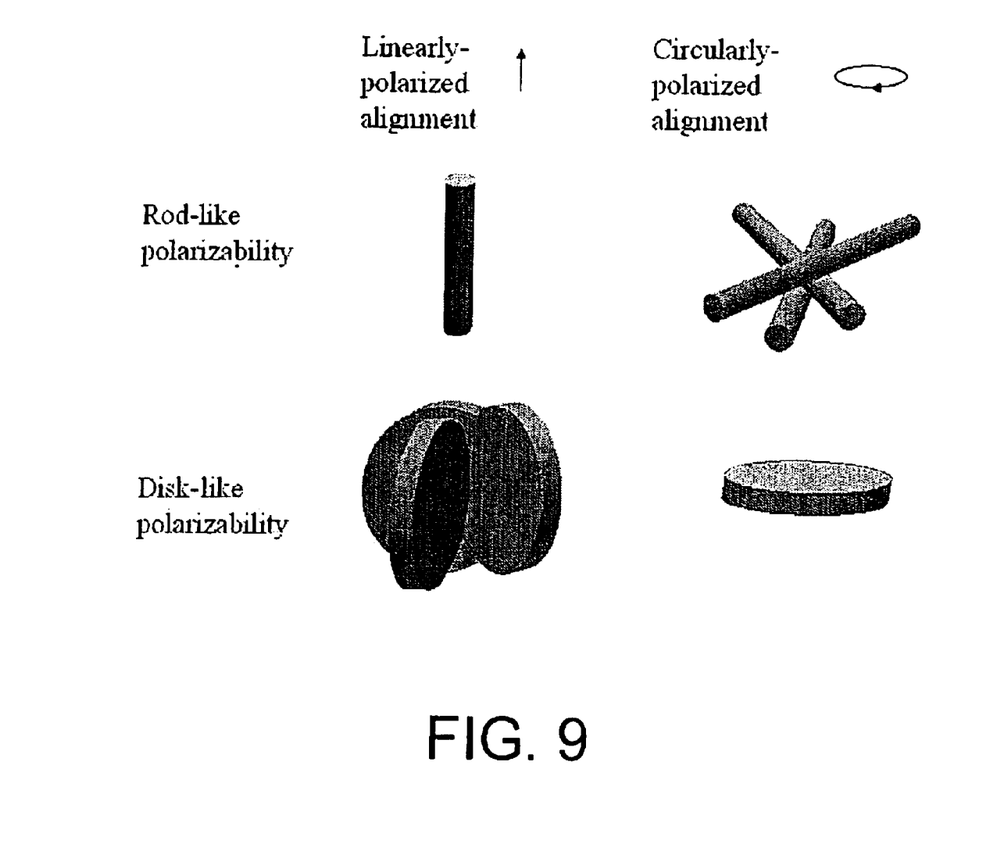
FIG. 9 are representations of different types of alignment for disk-like and rod-like polarizabilities in the presence of linearly and circularly polarized light.

It is seen that linear and circular polarization have the opposite effect on the alignment of molecules or n-mers. Changing the sign of $(\alpha_a-\alpha_b)$ also reverses the aligning effect of a given applied polarization. FIG. 9 summarizes the types of alignment behavior that are obtained in the two limiting cases of rod-like $(\alpha_a>>\alpha_b=\alpha_c)$ and disk-like $(\alpha_a<<\alpha_b=\alpha_c)$ polarizabilities, and in the limit of very strong alignment. For a rod-like polarizability, linearly polarized light induces the molecules to align with their rod axis parallel to the applied field ($K_x=0$, $K_y=0$, $K_z=1$), while circularly polarized light induces molecules to align with their rod axis in the xy plane, but with random azimuthal angle $\phi$ in that plane ($K_x=\frac{1}{2}$, $K_y=\frac{1}{2}$, $K_z=0$). For a disk-like polarizability, linearly polarized light induces the molecules to align with their disk axis perpendicular to the applied field, in the xy plane, with random azimuthal angle in that plane ($K_x=\frac{1}{2}$, $K_y=\frac{1}{2}$, $K_z=0$). Circularly polarized light induces molecules to align with their disk axis in the z-direction, perpendicular to the xy plane in which the applied field is rotating ($K_x=0$, $K_y=0$, $K_z=1$). Thus, it can be seen that linearly polarized fields are most effective in aligning n-mers with rod-like polarizabilities, while circularly polarized fields are most effective in aligning n-mers with disk-like polarizabilities.

The present method reveals a new approach to controlling crystal structure during nucleation of crystalline materials from solution. The use of polarization is much cleaner than other methods that require additives. In addition, polarization switching might lead to the formation of new, unknown and/or additional polymorphs of some substances, which can be characterized and used in the laboratory and/or industrial setting.

General

Nucleation in liquid solutions is a complex problem involving two components. This problem is of great theoretical and commercial importance, such as in industrial crystallization processes. The use of a light-induced process to cause nucleation and crystal growth to address this problem by obtaining novel or unexpected crystal structures can be used to prepare new polymorphs of materials or to obtain a known polymorph under different conditions than those under which the polymorphs usually are made.

The present invention provides a novel method for creating new or unexpected polymorphs of known substances by varying the polarization of the light incident on a solution. The polymorphs created with the present method can have internal crystal structures that are different than those currently known (the new polymorphs) or different than what would be expected by one of ordinary skill in the art without use of the present method (the unexpected polymorphs). Surprisingly, the polymorphs can be created essentially without chemically affecting or influencing the solution (that is, changing the chemistry of the solution). Practically, the present method is a non-chemical method of affecting the solution in a manner different than the prior art.

One embodiment of the present invention is a method for creating a polymorph by selecting by the polarization state of light incident on a supersaturated solution of a substance. This embodiment essentially comprises preparing a supersaturated solution of the substance in a solvent; selecting a polarization state of light necessary to induce nucleation; and subjecting the supersaturated solution to the light for a period of time so as to induce nucleation of a polymorph.

The supersaturated solution can be a product of another process or can be created by manipulation. Many processes commonly used in industry yield a product or a byproduct that is a supersaturated solution. Additionally, supersaturation of solutions can be achieved by methods including cooling, heating, solvent evaporation, and altering solvent composition and combinations thereof. It is also evident that products of industrial processes can be modified by techniques to further saturate a solution. Generally, the supersaturated solution is of a known substance, and it is desired to produce either known polymorphs or new polymorphs of that substance. One of ordinary skill in the art will understand that supersaturation of a solution can be accomplished from an array of methods and from combinations of such methods.

One such method obtaining of the supersaturated solution is a method of combining and heating the substance in a solute and solvent combination. When the solute and solvent are combined, the solute will dissolve in the solvent without further manipulation until a saturation point, i.e. the point at which the solution is at a dissolution-precipitation equilibrium between the solid substance and its dissolved form. Supersaturated solutions can be achieved by heating the saturated solution to an elevated temperature, typically known for specific substances, and holding it at that temperature for several days. Once the substance is completely dissolved in the solvent, solutions are slowly cooled to room temperature. Great care should be taken to exclude dust from samples, as dust can act as nucleating sites.

Once the supersaturated solution is created or exists by alternative means, the solution is irradiated by a light source of a selected polarization, which can be a laser, for a finite duration, to induce nucleation. Although exposure of the saturated solutions to laser pulses from the oscillator alone may not be sufficient to induce nucleation, with an amplifier added, nucleation can occur in a significantly shorter period of time, often within 10 to 20 seconds.

Once nucleation occurs, shortly thereafter crystals can be observed visually. Crystallization can be induced with a single pulse or a train of pulses lasting from approximately 0.01 second to approximately 1 hour. In some cases, the crystallites that are formed have the same structure as crystallites that form when the same solution spontaneously nucleates. One of ordinary skill in the art will be able to determine the duration of the exposure for optimal nucleation.

When light is incident on a molecule, the oscillating electric field of the light wave induces an oscillating electric dipole in the molecule. This induced dipole interacts with applied electric field resulting in a change of energy of the molecule. It is observed that the more intense the light, the stronger the associated electric field, and the greater the change in energy of the molecules. One of the best sources of intense light is a high-power pulsed laser, such as but not limited to a Q-switched Nd:YAG laser. This type of laser is preferred because it has a manageable and limited power range for the selection process.

One method of modifying a light source to a selected polarization is by use of a quartz quarter-wave retardation plate. This method could therefore be used to prepare new polymorphs of materials, which have not been observed, or to obtain a known polymorph under different conditions than those in which it is usually made. In effect, the light can be in a linear, circular or elliptical polarization state.

Thus, unexpectedly, in the present method a light source of a selected polarization, which is essentially not absorbed by the solution, induces solutions to crystallize into a polymorph not previously known and/or expected by the person of ordinary skill in the art. This effect allows the preparation of new polymorphs of materials that have not been observed, or of known polymorphs under conditions different than those in which they usually form. It is essential to note that the present invention facilitates the formation of new or unexpected polymorphs (having a new or unexpected internal crystal structure) and not of a known substance of different morphology (external crystal shape or appearance).

Figure 1:
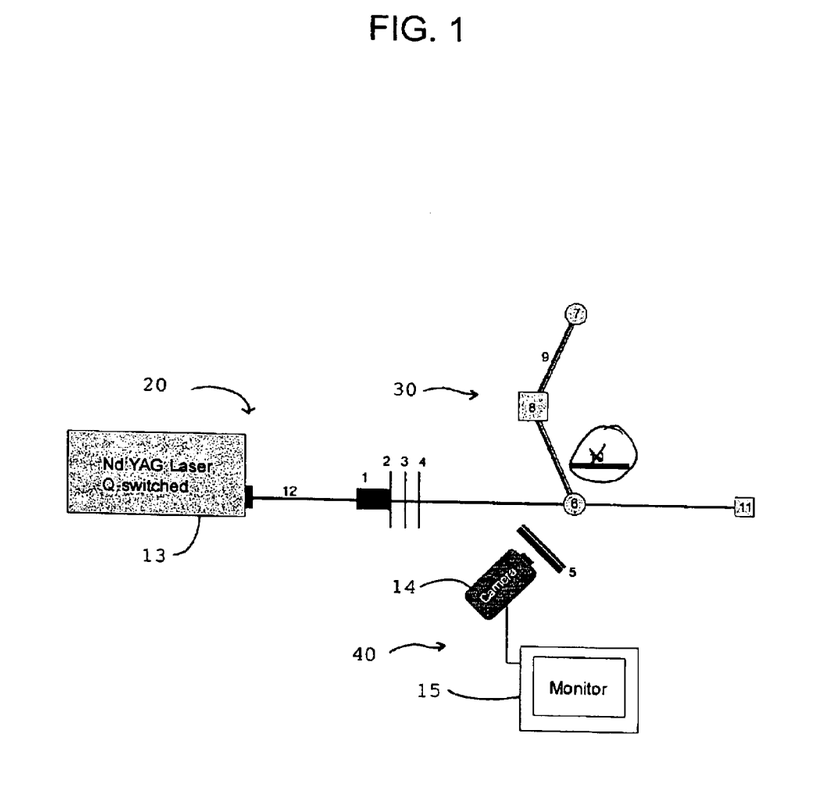
FIG. 1 is a representation of the basic arrangement of the laser system designed to achieve light with a circular polarization.

A sample apparatus for carrying out this process is shown schematically in FIG. 1. The apparatus generally comprises an optical table comprising a laser setup 20, a sample setup 30 and a monitoring setup 40 (comprising camera 14 with filter 5 and monitor 15). The sample setup 30 comprises a supersaturated solution 6 and/or a control sample 7 contained in an appropriate container such as a test tube, a magnetic stage 8, and a sample holder 9. In the apparatus shown in FIG. 1, laser pulses 12 emitted from the laser pass through the black tube 1, the aperture 2, end-the half wave plate 3 to enable the rotation of the plane of polarization, and a beam stopper 11. The polarized laser pulses 12 then pass through a calcite prism polarizer 4 to improve the purity of the linear polarization. A quarter wave plate can be placed after the polarizer 4 to switch the polarization. The resulting polarization can be linear, circular or elliptical. The laser 13 oscillator and amplifier typically are set at maximum power. With the example laser 13, the estimated peak intensities incident on the supersaturated solution are approximately 0.7 GW/cm$^2$. With the oscillator alone, peak intensities are about on third of this value. The use of a near-infrared laser is preferred, as this provides a narrow wavelength range for the selection process; however, other types of lasers are suitable for the general process.

The laser light pulses preferably at between 1 pulse and 100 pulses per second, and more preferably at 10 pulses per second, with the supersaturated solution being subjected to the laser light for a period of between 0.01 second and 1 hour, and preferably between 0.01 second and 60 seconds. The selection of both the number of pulses per hour and the length of time the supersaturated solution is subjected to the laser light are variable, depending on the type of solution being subjected to the process, and the desired result. One of ordinary skill in the art can select the desired pulse rate and time without undue experimentation. The now polarized laser pulses are directed at and pass through the supersaturated sample, inducing nucleation.

The supersaturated solution can be held in test tubes, or other appropriate holding containers, which can be placed in the path of the laser beam. The curvature of the test tube walls can cause some additional focusing of the light source; consequently, the solution can be subjected to light intensities somewhat higher than the light source. Use of flat walled holding containers can help eliminate this effect. However, it is possible to increase the intensity of the laser light by focusing with lenses or by amplifying the light, which may reduce the time to the onset of nucleation, may reduce the power of laser necessary to achieve the desired results, and/or may allow the nucleation of harder to nucleate substances.

EXAMPLES

The following examples illustrate preparation and processing methods of the invention. The following examples are not intended to limit or depart from the scope and spirit of the invention.

Figure 5:
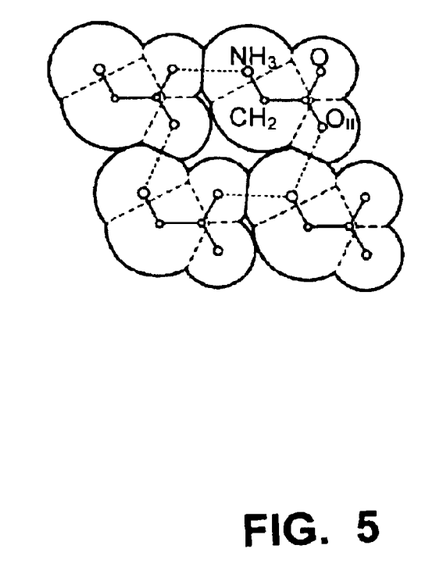
FIG. 5 is the structure of a glycine molecule and packing of molecules in alpha-glycine.
Figure 6:
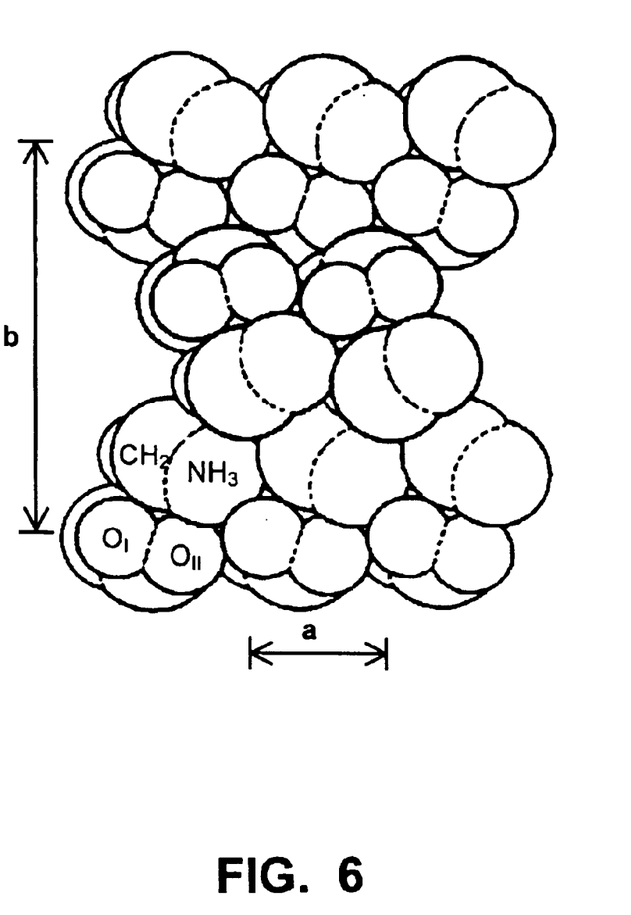
FIG. 6 is another view of the packing of molecules in alpha-glycine.
Figure 7:
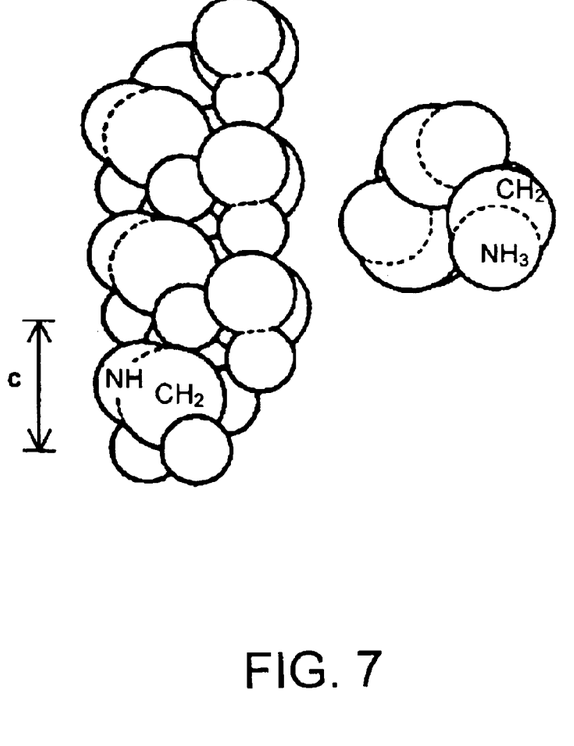
FIG. 7 shows two views of the packing of molecules in gamma-glycine.

One example of the present method is with aqueous solutions of the amino acid glycine. Glycine is known to form at least three different polymorphs under different conditions. The polymorph that normally forms from neutral aqueous solution is called the alpha form. FIGS. 5 and 6 show a representation of the known crystal structure of alpha-glycine. Another form of glycine, known as the gamma form, forms from acidic or basic aqueous solutions. FIG. 7 shows a representation of the known crystal structure of gamma-glycine. Glycine solutions that are not exposed to radiation always crystallize into the alpha polymorph. However, it has been found through the present method that plane (linear) polarized light induces the formation of the gamma glycine polymorph, and circular polarized light induces the formation of the alpha glycine polymorph. This previously was unknown and certainly not expected.

Another example of the present method is with aqueous solutions of the amino acid L-alanine, whose chemical structure differs from glycine. L-Alanine is known to have only one polymorph. Subjecting an aqueous L-alanine solution to the present method resulted in an unexpected and unknown polymorph. The unknown and unexpected L-alanine polymorph was verified with x-ray diffraction, which produced a strong signal at 19.98, which is a polymorph not known to occur in L-alanine solutions. It has been found using the present invention that plane (linear) polarized light induces the formation of a new polymorph of L-alanine.

The present method is applicable to solutions other than glycine or alanine in water. Those of ordinary skill in the art can produce other supersaturated solutions of compounds in appropriate solvents without undue experimentation. For example purposes only, suitable compounds include, but are not limited to, pharmaceuticals, amino acids, peptides, proteins, carbohydrates, amines, alkanes, alkenes, alkynes, aromatics, heterocyclic compounds, alcohols, organometallics, carboxylic acids, and derivatives of these compounds. Also for example purpose only, suitable solvents include, but are not limited to, organic, inorganic, and supercritical solvents. Once a compound is selected for treatment under this method, an appropriate solvent can be selected by those of ordinary skill in the art without undue experimentation.

1. Formation of Glycine Polymorphs

The three polymorphs of glycine can be formed under different solution conditions. α-glycine is formed by spontaneous nucleation of pure aqueous glycine, while γ-glycine is formed from acetic acid or aqueous ammonia solution, or by the addition of compounds that inhibit the growth of α-glycine, such as racemic hexafluorovalene. The structure of α-glycine is shown in FIGS. 5 and 6 and the structure of γ-glycine is shown in FIG. 7. The α-glycine structure consists of hydrogen-bonded double layers, whose basic unit is a cyclic hydrogen-bonded dimer (two antiparallel glycine molecules). The γ-glycine structure consists of helical chains of roughly parallel glycine molecules. These chains are hexagonally packed via lateral hydrogen bonds. In aqueous solution, each glycine molecule exists in the form of a zwitterion, in which a proton is transferred from the carboxyl to the amine group ($^+NH_3CH_2COO^-$).

The growth mechanism of α-glycine is probably based on the addition of cyclic dimers. In acidic or basic solution, the zwitterions gain or lose protons respectively, making cyclic dimer formation less favorable, thus inhibiting the growth of α-glycine. β-glycine can be formed by precipitation from ethanol-water mixtures. Although α-glycine forms spontaneously from aqueous solution, γ-glycine is the most stable polymorph at room temperature, an indication that the nucleation of glycine is kinetically rather than thermodynamically controlled.

Using near-infrared light having linear polarization, the laser-induced nucleation of glycine unexpectedly produced the γ-polymorph, while identical solutions allowed to nucleate spontaneously, always produce the α-polymorph. Using near-infrared light having circular polarization, the laser-induced nucleation of glycine always produces the α-polymorph.

Supersaturated solutions of glycine in water, with concentrations ranging from 3.7 M to 3.9 M, were prepared by combining appropriate amounts of solid glycine with 2 g of water in 1.3-cm diameter Pyrex test tubes with screw-on caps. Great care was taken to exclude dust from samples. Supersaturation was achieved by heating the samples in an ultrasonic bath at 50 C, and holding them at that temperature until the glycine was completely dissolved. The solutions were then slowly cooled to room temperature (21 C, $c_{sat}$= 2.69 M, where $c_{sat}$ is the concentration of a saturated solution). Solutions prepared in this way lasted for several weeks before spontaneously nucleating. Spontaneously nucleated crystals were always the α-polymorph.

Solutions aged from 3 to 8 days were exposed for one minute to the 1064 nm wavelength radiation of a Quanta-ray DCR-1 Q-switched Nd:YAG laser oscillator-amplifier system set at maximum output power. This laser produces a 10-pps train of 9-ns laser pulses. The beam produced by the laser is annular and has approximately linear polarization. A portion of the annular beam with approximately constant intensity was selected by passing the beam though a 2-mm diameter circular aperture. The intensity of the light incident on the sample solution is estimated to be 0.7 (±10%) $GW/cm^2$. A Glan-Thompson polarizer also was placed in the beam path to improve the purity of the linear polarization of the laser output.

To produce light having circular polarization, a quartz quarter-wave retardation plate at 1064 nm was used. The wave plate orientation was optimized by temporarily reflecting a beam back through the wave plate and polarizer. The best orientation was obtained when the intensity of the light transmitted back through the polarizer was minimized. The ratio of the full beam intensity to this minimized back-reflected intensity was 100:1, which corresponds to a purity of circular polarization of about 100:1.

Figure 8:
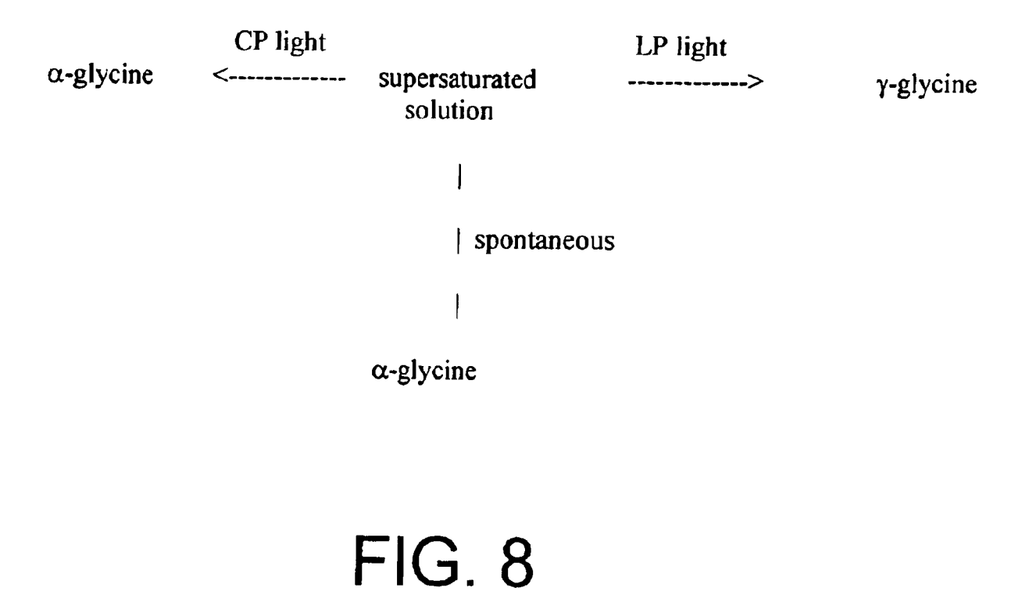
FIG. 8 represents the polymorphs of glycine obtained through spontaneous nucleation, circular polarization nucleation, and linear polarization nucleation.

Aged supersaturated solutions were exposed to laser pulses of either linear or circular polarization. In either case, about 30 minutes after exposure, small macroscopic crystals of glycine could be seen either sitting on the bottom or floating on the meniscus of the solution. These crystals were allowed to grow before removal from solution. All crystals were recovered from the mother liquor using vacuum filtration. Dried crystals were crushed and analyzed using powder x-ray diffraction. When the laser had linear polarization, γ-glycine was always obtained, whereas when the laser had circular polarization, α-glycine was always obtained, as shown in FIG. 8.

Figure 2:
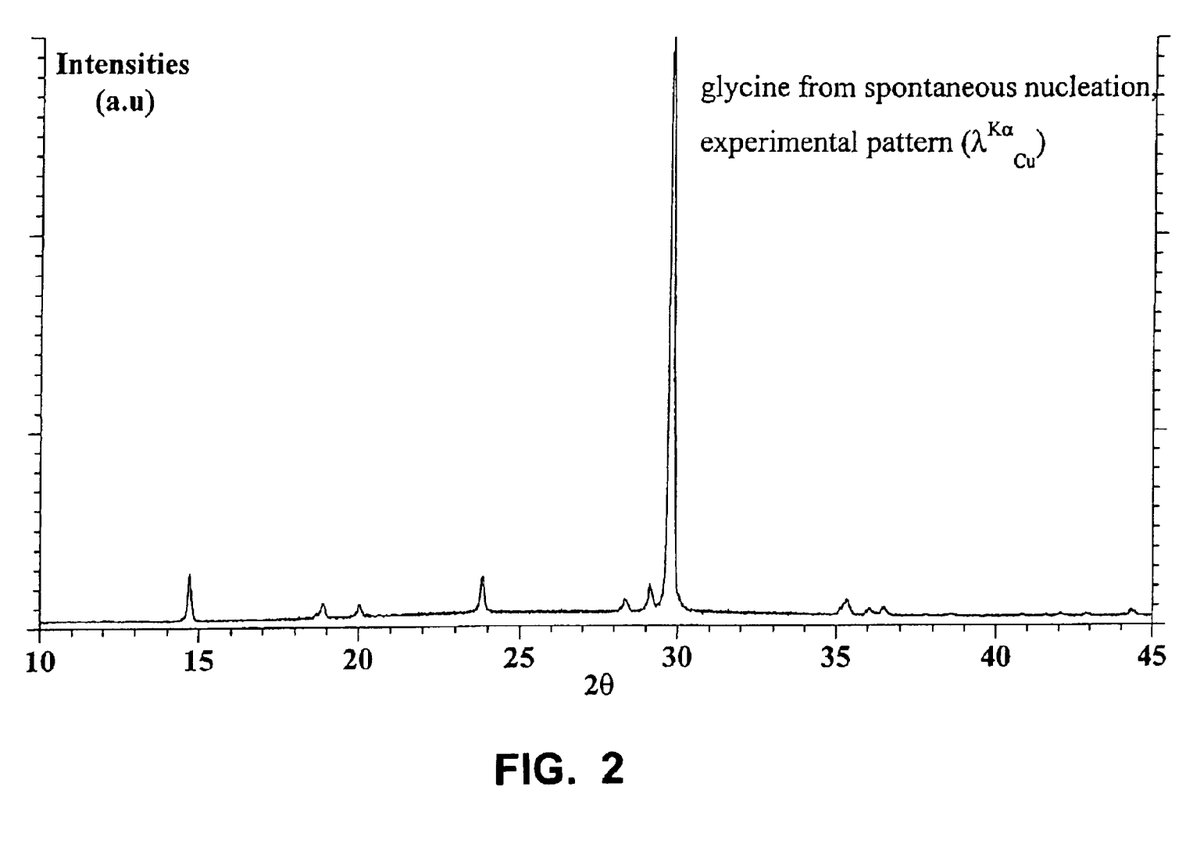
FIG. 2 is the x-ray powder diffraction pattern for glycine obtained from the spontaneous nucleation of a supersaturated aqueous glycine solution.
Figure 3:
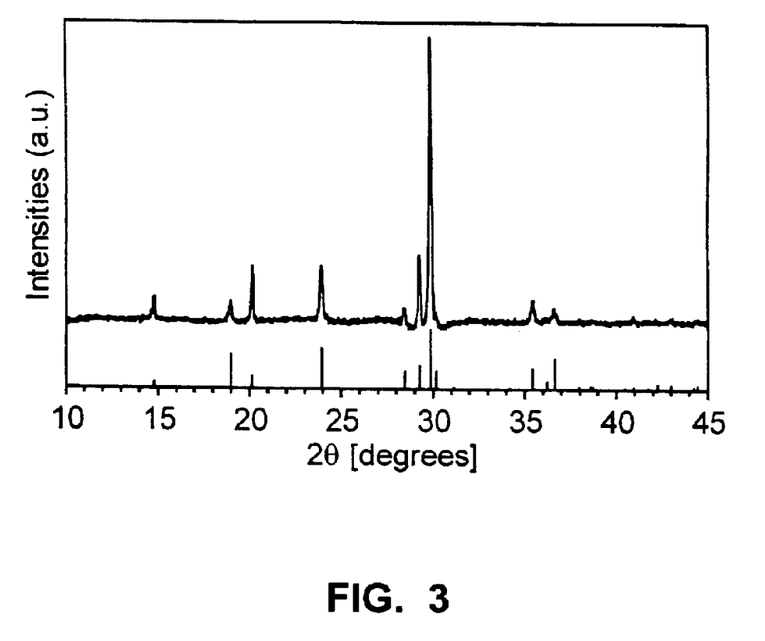
FIG. 3 is the x-ray powder diffraction pattern of crystals obtained from the laser-induced nucleation of a supersaturated aqueous glycine solution with circular polarization.
Figure 4:
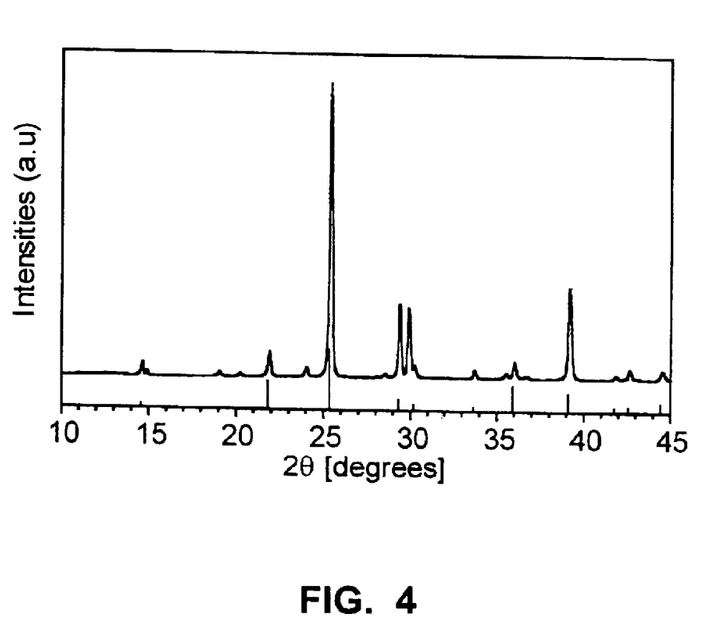
FIG. 4 is the x-ray powder diffraction pattern of crystals obtained from the laser-induced nucleation of a supersaturated aqueous glycine solution with linear polarization.

As shown in FIG. 3, the x-ray peaks obtained from crystals resulting from the laser-induced nucleation of a supersaturated aqueous glycine solution using circular polarization matched those of the alpha-polymorph of glycine. As shown in FIG. 4, the x-ray peaks obtained from crystals resulting from the laser-induced nucleation of a supersaturated aqueous glycine solution using linear polarization matched those of the gamma-polymorph of glycine. It was been found that suitable laser illumination times are from approximately 0.1 second to approximately 1 hour using a laser operating at 10 pulses per second. FIG. 2 is the x-ray diffraction pattern obtained from these control crystals. As can be seen, the x-ray diffraction pattern of FIG. 2 indicates the presence of alpha-glycine and no gamma-glycine.

2. Formation of L-Alanine Polymorph.

Supersaturated alanine with concentration of 40% was prepared using the procedure described above and aged for 5 days. Nucleation was induced by short pulses from the laser using linear polarization such as described above for glycine. Visible crystals were produced of a bipyramidal appearance in times ranging from 10 to 60 minutes. The x-ray diffraction pattern was observed to have an intense signal at 19.98 (2θ), which is absent from the x-ray diffraction pattern of the known form of alanine polymorphism. Hence, a crystal of unknown and unexpected polymorphism was created by this method. The complete powder x-ray diffraction analysis for this example is:

| 2Θ | Intensity |
| --- | --- |
| 14.32 | 3.5013 |
| 16.30 | 9.066 |
| 19.98 | 100 |
| 20.40 | 13.67 |
| 20.58 | 11.49 |
| 21.94 | 12.526 |
| 26.12 | 58.669 |
| 26.66 | 7.2857 |
| 27.115 | 8.5958 |
| 28.86 | 17.26 |
| 28.92 | 11.175 |
| 31.48 | 35.848 |
| 32.06 | 4.9252 |
| 32.26 | 5.8888 |
| 32.34 | 5.9162 |
| 38.38 | 3.9167 |
| 38.46 | 4.2637 |
| 40.62 | 7.797 |
| 42.04 | 3.3918 |

This x-ray pattern is not the same pattern reported for the single known crystal form of alanine.

This experimental procedure is applicable to solutions other than glycine and L-alanine in water. Those of ordinary skill in the art can produce other supersaturated solutions of compounds in appropriate solvents without undue experimentation.

The above description sets forth the best mode of the invention as known to the inventors, and is for illustrative purposes only, as it is obvious to one skilled in the art to make modifications to this process without departing from the spirit and scope of the invention and its equivalents as set forth in the appended claims. The use of glycine and L-alanine for the experimental portion of this specification is for illustrative and exemplary purposes only, as it is clear to one of ordinary skill in the art that the procedure and results disclosed and claimed in this specification can be performed for other compounds with polymorphs without undue experimentation.

What is claimed is:

1. A method of preparing a crystal polymorph, comprising the steps of:
   a. preparing a supersaturated solution of a known substance;
   b. selecting a polarization state of light to induce the onset of nucleation of crystals of the polymorph of the known substance from the supersaturated solution; and
   c. subjecting the supersaturated solution to the light for a period of time so as to induce the onset of nucleation of the crystals of the polymorph, wherein the known substance is not urea or alumina hydrate and the polymorph is used as a seed material to create larger amounts of the polymorph to be used in known processes.

2. The method of preparing a crystal polymorph as claimed in claim 1, wherein the supersaturated solution is aged for a period of 1 hour to 200 hours.

3. The method of preparing a crystal polymorph as claimed in claim 1, wherein the light is at most minimally absorbed by the supersaturated solution.

4. The method of preparing a crystal polymorph as claimed in claim 1, wherein the wavelength of the light is near infrared.

5. The method of preparing a crystal polymorph as claimed in claim 1, wherein the wavelength of the light is 1064 nm.

6. The method of preparing a crystal polymorph as claimed in claim 1, wherein the light has linear polarization.

7. The method of preparing a crystal polymorph as claimed in claim 1, wherein the light has circular polarization.

8. The method of preparing a crystal polymorph as claimed in claim 1, wherein the light has elliptical polarization.

9. The method as claimed in claim 1, wherein supersaturation is achieved by a method selected from the group consisting of cooling, heating, solvent evaporation, and altering solvent composition.

10. The method as claimed in claim 9, wherein the solvent is selected from the group consisting of organic solvents, inorganic solvents, and supercritical solvents.

11. The method as claimed in claim 1, wherein the substance is selected from the group consisting of pharmaceuticals, amino acids, peptides, proteins, carbohydrates, amines, alkanes, alkenes, alkynes, aromatics, heterocyclic compounds, alcohols, organometallics, and carboxylic acids.

12. The method as claimed in claim 1, wherein the light is a laser light and the laser light is pulsed.

13. The method as claimed in claim 12, wherein the laser light is pulsed at between 1 and 100 pulses per second.

14. The method as claimed in claim 13, wherein the laser light pulses at 10 pulses per second.

15. The method as claimed in claim 1, wherein the light is a laser light and the supersaturated solution is subjected to the laser light for a period of between 0.01 second and 1 hour.

16. The method as claimed in claim 15, wherein the supersaturated solution is subjected to the laser light for a period of between 0.01 second and 60 seconds.

17. A method of preparing a crystal polymorph, comprising the steps of:
   a. preparing a supersaturated solution of a known substance;
   b. aging the supersaturated solution for a period of 1 hour to 200 hours;
   c. subjecting the supersaturated solution to the light from a near-infrared laser emitting light at an elliptical polarization state for a period of time so as to induce the onset of nucleation of the crystals of the polymorph, wherein the known substance is not urea or alumina hydrate and whereby the selected polarization state of light controls the polymorph structure of the crystal.

18. The method of preparing a crystal polymorph as claimed in claim 17, wherein the wavelength of the light is 1064 nm.

19. The method of preparing a crystal polymorph as claimed in claim 18, wherein the power of the light is between 0.1 GW/cm$^2$ and 10 GW/cm$^2$.

20. The method as claimed in claim 17, wherein the laser light is pulsed at between 1 to 100 pulses per second.

21. The method as claimed in claim 20, wherein the laser light pulses at 10 pulses per second.

22. The method as claimed in claim 21, wherein the supersaturated solution is subjected to the laser light for a period of between 0.01 second and 1 hour.

23. The method as claimed in claim 22, wherein the supersaturated solution is subjected to the laser light for a period of 0.01 second and 60 seconds and the light is at most minimally absorbed by the supersaturated solution.

24. The method as claimed in claim 20, wherein supersaturation is achieved by a method selected from the group consisting of cooling, heating, solvent evaporation, and altering solvent composition.

25. The method as claimed in claim 24, wherein the solvent is selected from the group consisting of organic solvents, inorganic solvents, and supercritical solvents.

26. A method of preparing a crystal polymorph from a known substance, comprising the steps of:
   a. preparing a supersaturated solution of the known substance;
   b. aging the supersaturated solution for a period of 1 hour to 200 hours;
   c. selecting a polarization state of laser light to induce the onset of nucleation of crystals of the crystal polymorph of the known substance from the supersaturated solution, wherein the light is at most minimally absorbed by the supersaturated solution; and
   d. subjecting the supersaturated solution to the laser light for between 0.01 second and 1 hour so as to induce the onset of nucleation of the crystals of the polymorph, wherein the known substance is not urea or alumina hydrate wherein the polymorph is used as a seed material to create larger amounts of the polymorph to be used in known processes, and whereby the selected polarization state of light controls the polymorph structure of the crystal.

27. The method as claimed in claim 26, wherein the laser light is pulsed at between 1 and 100 pulses per second.

28. The method as claimed in claim 27, wherein the laser light pulses at 10 pulses per second.

29. The method as claimed in claim 28, wherein the supersaturated solution is subjected to the laser light for a period of between 0.01 second and 60 seconds.

30. The method as claimed in claim 26, wherein the substance is selected from the group consisting of pharmaceuticals, amino acids, peptides, proteins, carbohydrates, amines, alkanes, alkenes, alkynes, aromatics, heterocyclic compounds, alcohols, organometallics, and carboxylic acids.

31. The method as claimed in claim 30, wherein supersaturation is achieved by a method selected from the group consisting of cooling, heating, solvent evaporation, and altering solvent composition.

32. The method as claimed in claim 31, wherein the solvent is selected from the group consisting of organic solvents, inorganic solvents, and supercritical solvents.

33. The method of preparing a crystal polymorph as claimed in claim 30, wherein the wavelength of the light is near infrared.

34. The method of preparing a crystal polymorph as claimed in claim 33, wherein the wavelength of the light is 1064 nm.

35. The method of preparing a crystal polymorph as claimed in claim 26, wherein the laser light has a polarization state selected from the group consisting of linear polarization, circular polarization, and elliptical polarization.

36. The method of preparing a crystal polymorph as claimed in claim 35, wherein the light has linear polarization.

37. The method of preparing a crystal polymorph as claimed in claim 35, wherein the light has circular polarization.

38. The method of preparing a crystal polymorph as claimed in claim 35, wherein the light has elliptical polarization.

39. The method as claimed in claim 26, wherein the polymorph is used as a substitute for known polymorphs made under known conditions.

40. A method of preparing a crystal polymorph, comprising the steps of:
   a. preparing a supersaturated solution of a known substance and aging the supersaturated solution for a period of 1 hour to 200 hours;
   b. selecting a polarization state of light to induce the onset of nucleation of crystals of the polymorph of the known substance from the supersaturated solution; and
   c. subjecting the supersaturated solution to the light for a period of time so as to induce the onset of nucleation of the crystals of the polymorph, wherein the wavelength of the light is 1064 nm, the known substance is not urea or alumina hydrate, the light is at most minimally absorbed by the supersaturated solution and the polymorph is used as a seed material to create larger amounts of the polymorph to be used in known processes, and whereby the selected polarization state of the light controls the polymorph structure of the crystal.

41. The method of preparing a crystal polymorph as claimed in claim 40, wherein the polymorph is used as a substitute for known polymorphs made under known conditions.

42. The method of preparing a crystal polymorph as claimed in claim 40, wherein supersaturation is achieved by a method selected from the group consisting of cooling, heating, solvent evaporation, and altering solvent composition.

43. The method of preparing a crystal polymorph as claimed in claim 42, wherein the solvent is selected from the group consisting of organic solvents, inorganic solvents, and supercritical solvents.

44. The method of preparing a crystal polymorph as claimed in claim 43, wherein the substance is selected from the group consisting of pharmaceuticals, amino acids, peptides, proteins, carbohydrates, amines, alkanes, alkenes, alkynes, aromatics, heterocyclic compounds, alcohols, organometallics, and carboxylic acids.

45. The method of preparing a crystal polymorph as claimed in claim 40, wherein the light is a laser light and the laser light is pulsed.

46. The method of preparing a crystal polymorph as claimed in claim 45, wherein the laser light is pulsed at between 1 and 100 pulses per second.

47. The method of preparing a crystal polymorph as claimed in claim 45, wherein the laser light pulses at 10 pulses per second.

48. The method of preparing a crystal polymorph as claimed in claim 45, wherein the supersaturated solution is subjected to the laser light for a period of between 0.01 second and 1 hour.

49. The method of preparing a crystal polymorph as claimed in claim 45, wherein the supersaturated solution is subjected to the laser light for a period of between 0.01 second and 60 seconds.

* * * * *